United States Patent [19]

Csiki

[11] Patent Number: 4,608,217

[45] Date of Patent: Aug. 26, 1986

[54] METHOD FOR THE PRODUCTION OF AN EAR PLUG

[75] Inventor: Kalman Csiki, Landskrona, Sweden

[73] Assignee: Gullfiber AB, Billesholm, Sweden

[21] Appl. No.: 656,899

[22] Filed: Oct. 2, 1984

Related U.S. Application Data

[62] Division of Ser. No. 403,657, May 20, 1982, Pat. No. 4,498,469.

[30] Foreign Application Priority Data

Oct. 22, 1980 [SE] Sweden ............................ 8007422

[51] Int. Cl.⁴ .................. B29C 63/04; B29C 63/22
[52] U.S. Cl. ................................. 264/249; 264/292; 264/313; 523/121; 128/151; 128/152
[58] Field of Search ............... 264/510, 511, 516, 249, 264/292, 313, 920; 523/121; 128/151, 152

[56] References Cited

U.S. PATENT DOCUMENTS

| | | |
|---|---|---|
| 2,672,863 | 3/1954 | Leight . |
| 2,692,221 | 10/1954 | Bihler . |
| 2,785,675 | 3/1957 | Berkman . |
| 2,785,676 | 3/1957 | Berkman . |
| 2,888,921 | 6/1959 | Nielson . |
| 3,729,892 | 5/1973 | Aslund . |
| 3,736,929 | 6/1973 | Mills . |
| 3,771,521 | 11/1973 | Kittredge . |
| 3,791,385 | 2/1974 | Davis et al. . |
| 3,842,166 | 10/1974 | Bucalo . |
| 3,872,559 | 3/1975 | Leight . |
| 3,896,801 | 7/1975 | Grout . |
| 4,053,051 | 10/1977 | Brinkhoff . |
| 4,089,332 | 5/1978 | Rose . |
| 4,094,315 | 6/1978 | Leight . |
| 4,160,449 | 7/1979 | Wade . |
| 4,215,683 | 8/1980 | Lundin et al. . |
| 4,472,342 | 9/1984 | Carr ..................... 264/510 |

FOREIGN PATENT DOCUMENTS

| | | |
|---|---|---|
| 1929431 | 12/1970 | Fed. Rep. of Germany . |
| 619389 | 3/1927 | France . |
| 220585 | 5/1968 | Sweden . |
| 341238 | 12/1971 | Sweden . |
| 341784 | 1/1972 | Sweden . |
| 369838 | 9/1974 | Sweden . |
| 419065 | 7/1981 | Sweden . |
| 1016222 | of 0000 | United Kingdom . |
| 578613 | 7/1916 | United Kingdom . |
| 438283 | 11/1935 | United Kingdom . |
| 527560 | 10/1940 | United Kingdom . |

Primary Examiner—Lucille M. Phynes
Attorney, Agent, or Firm—Burns, Doane, Swecker & Mathis

[57] ABSTRACT

The ear plug (40) includes an elongate body with a rounded tip portion and of an elastic material enveloped by a deep-drawn sheath (41) of thin flexible plastics film material. Rearwardly the plug preferably has a neck portion from which the sheath projects in the form of a stiffer collar or flange. Production of the ear plug includes deep-drawing a thermoplastic film or foil into a sheath with desired thickness distribution, and filling the sheath with elastic material (53). Filling may take place simultaneously with deep-drawing, the body of elastic material constituting a die for deep-drawing in a forming hole (45), or after the deep-drawing. In the latter case, an elastic die body is used to advantage, the shape of which generally corresponds to that of the finished plug, for deep-drawing in a forming hole suited to the die body.

8 Claims, 6 Drawing Figures

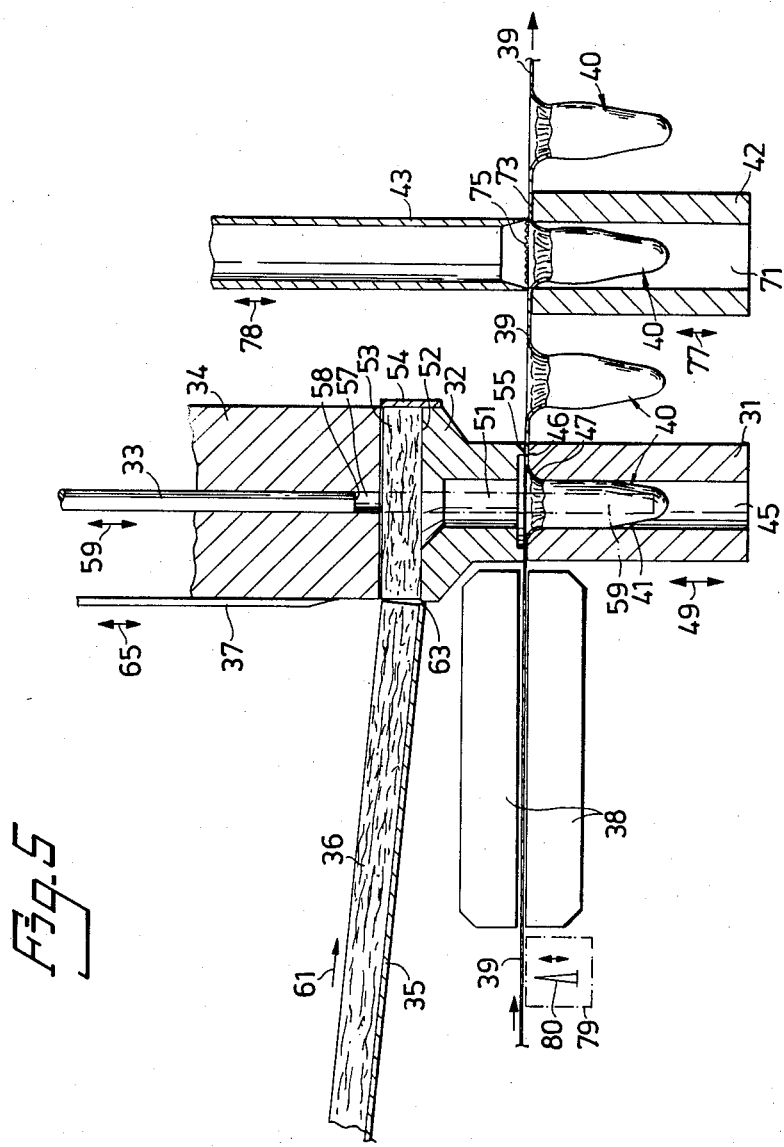

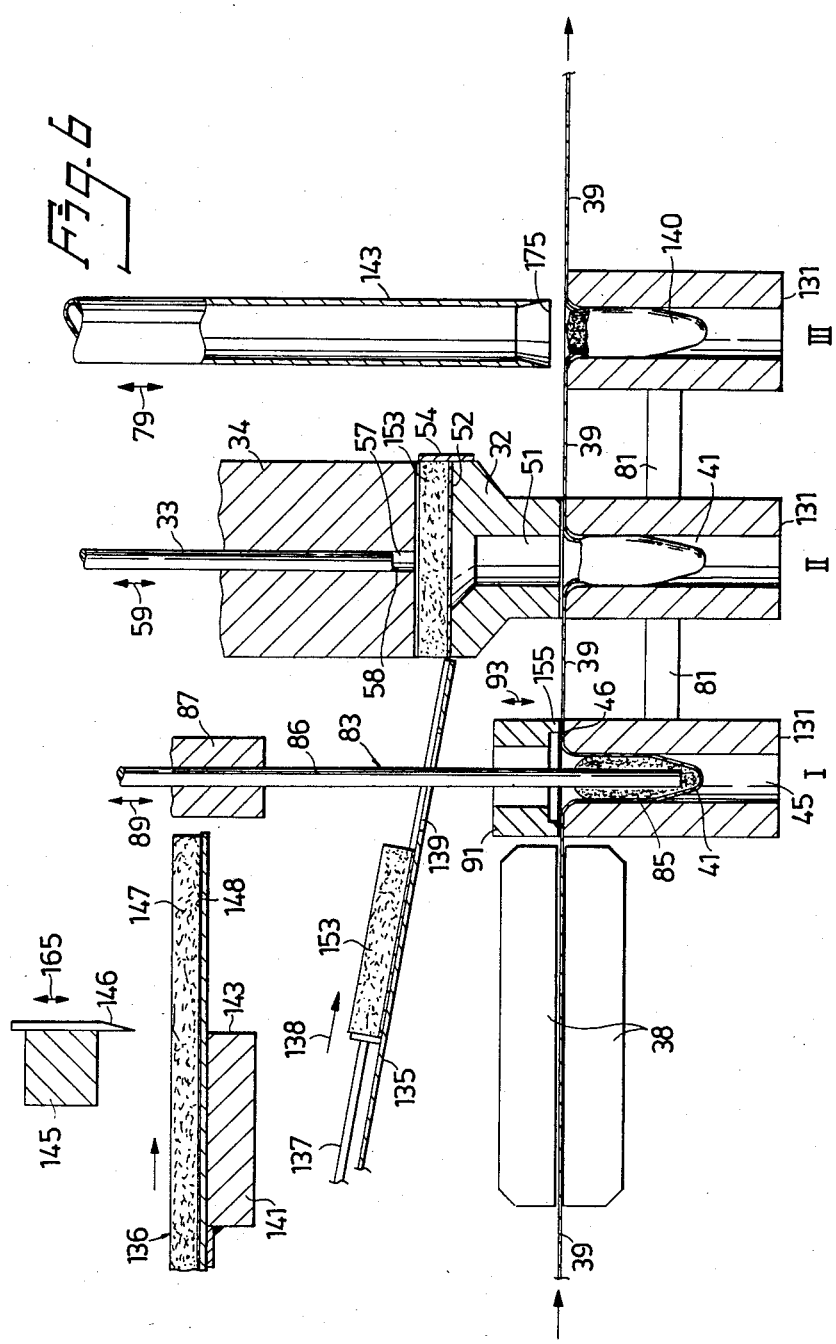

METHOD FOR THE PRODUCTION OF AN EAR PLUG

This application is a division of application Ser. No. 403,657 filed May 20, 1982 now U.S. Pat. No. 4,498,469 issued Feb. 12, 1985.

TECHNICAL FIELD

The present invention relates to sound-damping ear plugs of the kind including an elongate body of elastic material surrounded by a sheath of flexible material, which is intended to be inserted in the auditory meatus or canal of an ear, and to the production of such ear plugs.

PRIOR ART

Ear plugs of the kind mentioned above, where the sheath or casing comprises a moulded rubber material or the like, have been known for a very long time. In such cases, the sheath is comparatively thick and made so that it is yielding but simultaneously has a tendency to return to its predetermined shape in an unloaded condition. The ear plugs can have a tapering or rounded tip or forward portion, and at their rear portion they can include or be provided with a specially formed gripping or retaining portion, intended for accommodation in the external ear. Examples of ear plugs of this kind are disclosed in U.S. Pat. No. 2,785,675 and DE OS No. 1,929,431.

Ear plugs of the kind mentioned in the introduction, where the sheath comprises a thin plastic film are also already known.

The U.S. Pat. No. 3,771,521 discloses an ear plug comprising a cylindrical body made from a tacky polymeric material (silicone putty) entirely enclosed in a plastics film sheet swept round the body, and fused to a knob at the rear end of the body.

In our Swedish Patent No. 7603411-5 there is described an ear plug comprising a body of mineral fibre material surrounded by a sheath of thin plastics film. The body comprises a substantially cylindrical portion, intended for insertion in the auditory meatus of an ear, and an expanded end portion intended for at least partially filling up the concha outside the auditory meatus after the plug has been inserted. The plastics film sheath is swept round the body so that longitudinal creases are formed in it, the plug being fixed by a circumferential heat weld being arranged in the film substantially at the juncture between the cylindrical portion and the expanded end portion.

OBJECT OF THE INVENTION

One object of the present invention is to provide a new ear plug of the kind mentioned in the introduction, in which the sheath comprises a thin flexible plastics material and which affords improved sound attenuation or damping properties as well as simplified handling.

An other object of the present invention is to provide a method and an apparatus enabling the production of an ear plug in accordance with the above in an advantageous mode.

SUMMARY OF THE INVENTION

The above-mentioned objects are achieved by the ear plug, as well as the method and apparatus for producing it being given the characterising features defined in the appended claims.

The inventive ear plug is thus distinguished in that the sheath is provided by deep-drawing a thermoplastic film or foil. Preferred plastics materials for the sheath are polyvinyl chloride (PVC), polyurethane (PUR) and particularly polyethylene (PE).

With regard to the plastics material it should have high values for tensile strength and elongation at break, and a relatively low value for the tensile yield. As far as possible, said values should be the same in different directions. In a preferred embodiment of the invention, the plastics material should furthermore have small recovery after drawing, i.e. small shrinkage after drawing. The use of a plastics material with similar properties lengthwise and crosswise is especially advantageous, since the material can be extensively deep-drawn (i.e. the general thickness of the sheath in the drawn portions can be very small) with retained capacity of the sheath to maintain the enclosed elastic material in the desired shape. The radially or transversely acting pressure from the elastic material kept in the sheath will namely not have the opportunity of giving rise to a break in the casing in any direction with notable low strength.

The utilization of plastics material with the properties mentioned above enables the initial use of thin films or foils, and to allow the thickness of the deep-drawn sheath, seen in general, to be very small with retained ability of the sheath to effectively enclose a large amount of elastic material, simultaneously as the hearing protection plug can be easily inserted in the auditory meatus of an ear, and on such insertion can extremely well adjust itself to, and close off the auditory meatus. A large amount of elastic material in combination with easy insertion in the auditory meatus as well as good adjustment thereto signifies very good sound damping properties and excellent comfort.

By the sheath being deep-drawn, it has been found possible to vary the thickness distribution of the sheath while taking into account the plastics material used, shape of the plug etc., as will be accounted for in detail hereinafter.

In accordance with the invention, at the rear of the plug the sheath can be thicker and include a collar or flange portion outwardly and transversely directed, which gives a stiffening effect advantageous for insertion, and also makes handling of the plug very simple. After insertion of the ear plug, the collar or flange portion is intended to lie adjoining the orifice of the auditory meatus and just outside the latter. The sheath thickness in the collar portion is suitably substantially equal to the original film or foil thickness.

As previously mentioned, the drawn portion of the sheath surrounding the elastic material has a very small thickness, which can typically be one or a few tens of $\mu$m.

In an alternative embodiment, the sheath can have a thickness over the actual tip portion of the rounded-off plug substantially exceeding the general thickness of the sheath in the drawn-out portions which surround the elastic material. The thickness of the sheath across the actual tip portion can approach the original film or foil thickness. An embodiment of this kind makes it possible to arrange holes or perforations at the plug tip without risk of the sheath easily rupturing thereby. Such holes or perforations can be desirable, e.g. from the aspect of pressure equilization.

The deep-drawn sheath can to advantageously have longitudinal rib-like zones with greater thickness than the main portion of the rest of it. It is particularly advantageous if these riblike zones connect a thicker collar portion and a thicker tip portion of the sheath so that a basket-like configuration is formed. This contributes to providing the plug with stiffness, which facilitates insertion of the plug in the auditory meatus without the accommodating ability of the plug thereto being affected unfavourably. The riblike zones do not need to have uniform thickness, e.g. they can have a thickness varying from tip portion to collar portion.

According to a first embodiment of an ear plug in accordance with the invention, the elongate body of elastic material has a tapering forward portion, which is substantially conical with a rounded-off tip, the sheath being thinner at this portion than at the rear portion of the body. The latter is generally outwardly curving or spool-shaped. In such a case the sheath advantageously forms a diameter-reduced neck portion on the plug at the rear end of the rear part of the body, in that the sheath goes into an outwardly directed collar or flange portion of the kind already mentioned. The tapering forward portion constitutes at least about 1/5, suitably between ¼ and about ½, typically about ⅓ of the total length of the body or plug up to the neck portion.

Typically the thickness of the sheath at the tapering forward portion can, at least at the tip area, be from one or some tens of $\mu$m to some hundreds of $\mu$m. At the rear portion of the body, and especially at the neck and flange portion, the sheath thickness can typically be between about 0.2 and about 0.6 mm, preferably about 0.3–0.45 mm.

The thickness of the sheath increases, preferably substantially continuously, from the tip of the plug to its rear portion. A uniformly increasing thickness distribution has been found to be advantageous. However, the sheath can also be very thin at the forward portion and gradually increase relatively slowly in thickness from the plug tip and rapidly increase in thickness in conjunction with the changeover from the forward portion to the rear portion. and at least substantially have attained full thickness where the plug has its geatest width. The sheath can be somewhat thicker still in the neck and collar portion.

An ear plug according to this first embodiment is particularly advantageous in conjunction with a sheath material which has pronounced shrinkage effect and/or nonuniform properties with respect to longitudinal and transverse direction. Substantial advantages are gained with the ear plug. The thin sheath on the tapering forward portion of the plug makes it extremely pliable during insertion into the auditory meatus of an ear. The thicker sheath on the rear portion of the plug makes it stiff enough not to be wrinkled or pressed together in a disadvantageous mode during insertion, although the general yielding property of the plug is not affected in any negative mode. The special configuration of the rear portion of the plug, in combination with the good pliability of its forward portion thus affords that the whole plug admirably accomodates itself to, and closes off the auditory meatus, and subsequently remains there safely with retained great comfort. The configuration of the plug also means that it needs solely to contain so much elastic material as is necessary for closing off the auditory meatus, and that the correct insertion of this material is enabled without the plug needing to be provided with any special, complicated gripping or holding means.

According to a second preferred embodiment of an ear plug in accordance with the invention, the elongate body of elastic material similarly has a forward tapering portion, whereas the rear portion of the body does not have an equally well-defined spool shape, i.e. it is substantially cylindrical. In this case, the sheath has substantially the same thickness over the whole of the drawn area, onto which joins a thicker collar or flange portion. The thickness of the sheath in the collar portion may typically be between about 75 $\mu$m and about 200 $\mu$m, preferably about 100 $\mu$m, and otherwise in the range of 5–10 $\mu$m. The forward portion in this embodiment is suitably somewhat shorter, typically about ¼ of the total body length.

When utilizing a thicker sheath portion at the tip portion itself, according to what has been described earlier (which is advantageous in conjunction with this embodiment) the thickness at the actual tip portion can typically be of the order of 80 $\mu$m. In this connection it has been found advantageous to utilize the previously described, stiffening, basket configuration for the sheath.

Ear plugs according to this second embodiment are especially advantageous in conjunction with a sheath material which does not have a pronounced shrinkage effect and which has the uniform properties in longitudinal and transverse directions.

This second plug embodiment also gives substantially the same advantages as accounted for the first embodiment, although the necessary stiffness for facilitating the insertion of the plug is obtained in a different mode, namely by more distinctly keeping together primarily the plug rear portion.

The elastic material can be fibrous and/or polymeric material, preferably mineral fibre material, and particularly so-called glass "down", possibly in combination with a core of polymeric material, especially foam plastics. Filler may be included. In conjunction with a core of polymeric material, the fibrous material is suitably present in the form of a layer surrounding the core and coming against the sheath. In a combination of this kind, the fibrous layer ensures very good engagement against the auditory meatus wall, while at the same time enabling the selection of material, e.g. the foam plastics material, with other factors in view, such as general sound-damping properties and cost.

The elastic material is preferably stratified and folded over or away from the tip portion of the plug. The material may constitute felt, web or sheet material folded back away from the tip of the plug and swept about the longitudinal axis thereof. The elastic material fills the sheath at least up to the neck portion of the plug.

Practical tests have shown that ear plugs in accordance with the invention afford extremely good sound damping properties. In comparison with ear plugs in accordance with our previously mentioned Swedish Pat. No. 7603411-5 (for which there is documentary evidence showing that they give very good sound damping) we have thus found that ear plugs according to the present invention afford substantial dampening increase at low frequencies (typically between 10 and 5 dB within the frequency range of 125–400 Hz) and give approximately just as good damping as said known plugs at higher frequencies. Since the damping increase is greatest at the lowest frequencies, and it is there that the need of damping is generally the greatest as well as the most difficult to achieve, the damping increase obtained in accordance with the present invention signifies a great advance.

The present invention also includes a method and apparatus for advantageous, preferred production of ear plugs of the kind discussed above.

The method in accordance with the invention is essentially distinguished in that a thermoplastics film or foil is deep-drawn to form a sleevelike sheath, preferably at least substantially corresponding to the desired plug shape, which is forwardly tapering and which has the desired sheath thickness distribution, and that the sheath is filed with elastic material.

The thickness distribution of the sheath can be influenced by the selection of film or foil (type and thickness), by suitably heating of the film or foil before deep-drawing (including graded heating of the area to be drawn), by selection of suitable drawing rate and by utilizing suitably formed die and/or mould. It has been found suitable, for example, when using a die to deep-draw the sheath, to allow the plastics film or foil freely to coact with the die in respect of the tapering forward portion of the sheath, but to guide the plastics film or foil into a cylindrical shape between die and a coacting encircling mould surface with respect to the rear portion of the sheath. The die may easily be given such a contact surface, and remaining conditions may be selected in such a manner that the sheath portion obtained over the actual tip portion of the body is not subjected to any deep drawing proper.

The previously discussed basket configuration can be achieved, for example, by sheath areas corresponding to the desired ribs being prevented from being drawn too much by having them subjected to friction and/or selective cooling. This can be achieved by a die body utilized for the deep-drawing having longitudinal portions which either are in the shape of ridges or are separated by walley-like portions.

In accordance with the invention, the deep-drawing can be done such that after heating and forming to a sheath the thermoplastic film or foil can shrink during cooling in the joining area between the sheath portion and the enveloping portions of the plastics film or foil, so that there is formed a neck portion with a reduced diameter at the portion of the sheath opposite a tip or forward portion. The shrinkage means that the plastics film or foil in the appropriate area at least substantially returns from a drawn, thinner condition to the initial condition in respect of its thickness. When deep-drawing is carried out so that the formed sheath will be thinnest at a rounded tip portion of the sheath and so that the sheath increases therefrom in thickness, substantially to attain the original film or sheet thickness at the rear portion of the sheath, the previously mentioned shrinkage effect is aided simultaneously as there is ensured the outwardly curved form of the rear portion of the finished plug after filling with elastic material.

According to a first implementation of the method in accordance with the invention, the plastics film or foil is deep-drawn to a sheath simultaneously as the elastic material is inserted therein. In particular, the deep-drawing is accomplished by the actual insertion of the elastic material. The elastic material is hereby suitably formed about the free end of a plunger into an elongate body, forming a die body, the plastics film or foil being subsequently deep-drawn by means of, and about the die body, whereafter the plunger is removed so that the elastic material remains in the sheath obtained. Forming of the die body takes place to advantage by a piece of elastic material in the form of a web, felt, sheet or the like, being gathered or swept round or backwards about the plunger. The die formed in this manner will have longitudinal portions of the kind allowing the provision of the basket configuration of the sheath.

According to a second implementation of the method in accordance with the invention, the plastics film or foil is first deep-drawn by means of a die having a shape substantially conforming to the shape of the final plug, and which at least has an elastic surface layer, whereafter the elastic material is inserted in the sheath obtained by deep-drawing after removal of the die. The insertion suitably takes place by forming the elastic material to an elongate body about the free end of a plunger after thereafter thrusting the elastic material by means of the plunger into the sheath obtained by deep-drawing. This forming of the elastic material also takes place advantageously by a piece of elastic material in the form of a web, felt, sheet or the like being swept round or backwards about the plunger. To facilitate thrusting into the sheath it is suitable to provide an outer layer on the body of plastic material having low friction in relation to the sheath. This layer can advantageously include fibrous material, such as mineral fibres. The rest of the elastic material can hereby also constitute such material as has high friction relative to the sheath, e.g. certain kinds of foam plastics.

It is to be emphasized that sweeping round, or gathering a substantially uniformly thick square piece of elastic material about a suitably dimensioned plunger for inserting the material in the sheath (at or after shaping the latter) means that after removing the plunger, the elastic material is given a distribution in the sheath which corresponds extremely well to a plug shape suitable for the present invention.

In the second implementation of the method in accordance with the invention, the elastic material can also be inserted in the formed sheath in the form of smaller bits or pieces. These pieces can suitably first be stored in a compressed condition inside a tube, a plunger or the like, which is thereafter taken down into the sheath, the pieces then being pressed out from the tube, plunger or the like through a suitable opening simultaneously as the tube, plunger or the like is removed from the sheath.

In sequential forming of plug sheaths (and filling elastic material therein) starting from strip-like plastics film or foil material, a sequence of interconnected ear plugs may be obtained, which allows simple handling, and from which an individual ear plug can be simply removed when needed, particularly if fractural zones are arranged in the plastics strip around the outer collar or flange edge of each ear plug.

The apparatus in accordance with the invention is essentially distinguished in that it includes means for deep-drawing a thermoplastics film or foil into a sheath and means for filling the sheath with elastic material. These deep-drawing means include a die means and a coacting mould or form means, means for heating the plastics film or foil, and means for providing the plastics film or foil between the die and mould means, the die and mould means being adapted to be brought into mutual engagement from either side of the heated plastics film or foil, so that the latter is drawn over the die means and formed into a sheath over said die means and against the mould means. The die and mould means are preferably formed such that the plastics film or foil is first deep-drawn freely over the die means, and thereafter also formed between the outer surface of the die means and the inner forming surface of the mould means. The plastics film or foil is hereby in friction contact with the die means and the mould means, and it is important for achieving the desired sheath thickness distribution that the drawing surface of the die means has low friction in respect of the plastics film or foil where the latter is to be drawn. It is also advantageous that the die means has at least some elasticity. The die means should have such lengths or on a rear portion be reduced in diameter and/or be so elastic that possible shrinkage effect of the drawn plastics film or foil is facilitated.

The mould means coacting with the die means can constitute a forming body with a cylindrical forming hole with a rounded edge at the form hole orifice in a contact surface for the plastics film or foil. This surface is suitably flat with extension at right angles to the axial direction of the forming hole. The forming hole is suitably a through-hole and has a diamter which is somewhat less than the greatest width of the finished ear plug (apart from the collar or flange), which is obtained when supplied elastic material expands after removal from the mould. The depth or length of the forming hole is at least equal to the rear portion of the finished plug. Means are suitably provided for holding the plastics film or foil during deep-drawing, said means clamping the film or foil against the contact surface about the mould orifice and at a distance therefrom such that possible shrinkage and collar formation can take place unhindered.

According to a first embodiment of the apparatus in accordance with the invention, the die means includes a plunger and means for providing the elastic material about the free end of the plunger, to form an elongate die body substantially corresponding to the plug body, whereby the plunger also constitutes said means for filling the formed sheath with elastic material, by the plunger being adapted for separation from said mould means after forming the sheath, while leaving the elastic material in the sheath. For shaping the die body a pre-shaping means is advantageously arranged above the mould means, the pre-shaping means having a forming through-hole, in time with the mould means forming hole and preferably with substantially the same diameter as the latter, the plunger being adapted for pressing a piece of elastic material down through the pre-shaping means (to form the die body by folding around the plunger) and further towards the plastics film or foil and down into the mould means. The pre-shaping means is preferably arranged immediately adjacent the mould means, said two means being disposed movable in relation to each other. So that the pre-shaping means can also constitute the previously mentioned clamping means for the plastics film or foil. Forming of the die body by folding a piece of elastic material in this way about a plunger end gives the die body a shape, especially a forward tapering portion, which advantageously permits drawing the plastics film or foil into a sheath with a thickness distribution desirable in accordance with the invention.

According to a second embodiment of the apparatus in accordance with the invention the die means includes a die body which has a shape generally corresponding to that of the finished plug, the body being elastic and preferably fibrous, at least in respect of an outer layer. In other words, the die body shall suitably have approximately the same properties as a die means obtained by the previously discussed folding of elastic material about a plunger end. Advantageously, the die body may comprise a soft felt material with an outward low-friction fibrous layer, and may include a forward conically tapering portion with a bluntly rounded tip, and a rear portion which is substantially cylindrical with a diameter somewhat larger than that of the forming hole. The length of the die body can be approximately equal to the length of the finished ear plug up to a possible neck portion or approximately equal to the total length of the finished ear plug. The die body being formed rearwardly in accordance with desired shaping of the neck and collar portion of the sheath. Means for filling the formed sheath with elastic material may in this second embodiment also include a plunger and a pre-shaping means, these having substantially the same general embodiment and function as in the apparatus according to the first embodiment.

If the plastics film or foil intended for forming the sheath includes superfluous material outside the collar or flange of the finished plugs after forming, the apparatus in accordance with the invention may include a stamping means for separating the superfluous material or for providing such fractural zones that an individual ear plug can easily be separated by hand, e.g. from a plastics film or foil strip containing a plurality of finished ear plugs. Such a stamping means can be adapted for coaction with a film or foil contact surface on a utilized mould means.

SHORT DESCRIPTION OF THE DRAWING

The invention will now be explained in more detail by means of embodiment examples while referring to the appended drawing, in which FIG. 1 is a schematic enlarged longitudinal sectional view of a first embodiment of an ear plug in accordance with the invention; FIG. 2 is a schematic enlarged longitudinal sectional view of a second embodiment of an ear plug in accordance with the invention; FIG. 3 is a schematic enlarged side view of a third embodiment of an ear plug in accordance with the invention; FIG. 4 is a schematic, enlarged longitudinal sectional view of the ear plug in FIG. 3; FIG. 5 is a schematic side view partially in section illustrating a principle construction of an apparatus in accordance with the invention, especially suitable for producing ear plugs of the general configuration illustrated in FIGS. 1 and 3; and FIG. 6 is a view, of the same kind as in FIG. 5, of an apparatus in accordance with the invention, especially suited for producing ear plugs of the general configuration shown in FIG. 2. The same reference denotations have been used in the figures for the same or mutally corresponding parts. In FIGS. 1, 2 and 4 the sheath thicknesses illustrated are not to scale, but are exaggerated with the object of clearly indicating the prevailing sheath thickness distributions.

DESCRIPTION OF EMBODIMENTS

Figure 1:
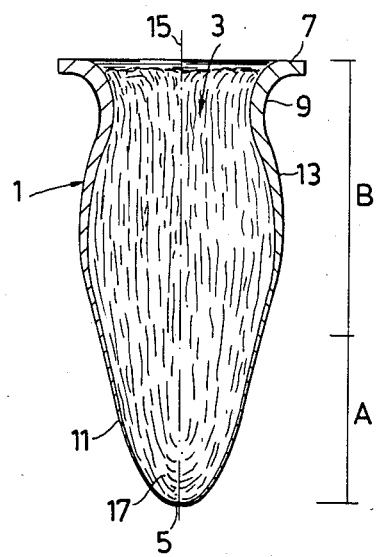

The ear plug illustrated in FIG. 1 comprises a deep-drawn sheath 1, which is of a thin film, e.g. of PVC-plastics, and which has the shape of an upwardly open axially elongate container, and an elastic, fibrous body 3 of mineral fibre material in the form of so-called glass down enclosed in the sheath. The plug has a lower, or in respect of insertion in an ear, a forward portion A and an upper or rearward portion B. The forward portion A is substantially conically tapering and terminates in a blunt rounded tip 5. The rear portion B of the plug is generally weakly spool-shaped or outwardly curving, apart from the sheath 1 projecting out in the form of a collar or flange 7 at the rear end of the plug, to form a neck portion 9 with reduced diameter. The sheath 1 is not the same over the whole plug, but has a thickness which is substantially different at the forward portion A of the plug compared with the rest of the plug. The forward portion of the sheath corresponding to the plug portion A thus has a thickness, which at the tip 5 is typically about 10–15 μm, and otherwise somewhat increasing but of the same order of magnitude. The rear portion 13 of the sheath typically has a thickness of about 0.1–0.3 mm, with the greatest thickness at the flange or collar 7. At the changeover to the forward portion 11 of the sheath, the thickness decreases relatively rapidly to the value applicable for said forward portion. This rapid thickness reduction begins below the area of the plug where it has its greatest width or diameter (apart from the flange or collar 7).

The sheath 1 has a smooth, slippery, outer surface which will give small friction against the auditory meatus wall when being inserted in an ear.

The flange or collar 7 projects transversally outwards and will constitute a grip or handling portion facilitating the general handling of the ear plug, as well as an annular "pressure plate" against which pressure can be applied by means of a finger tip in conjunction with pressing the ear plug into the auditory meatus of an ear. The flange or collar 7 will hereby also constitute in an advantageous manner a stop coacting with the parts of the exterior ear surrounding the auditory meatus opening, whereby a suitable position for the ear plug is ensured.

The fibrous body 3 substantially fills the sheath 1, i.e. up to and including the neck portion 9. The fibre material in the body 3 has a stratified structure, the plane of stratification being substantially parallel to the axis 15 of the plug. The material strata are folded over or back away from the tip 5 of the plug (as indicated at 17). The body 3 constituted a piece of fibre felt, which is folded over and back away from the tip 5 about the axis 15 of the plug. The stratified structure and elasticity of the fibrous material ensures that the sheath is well filled out and that the plug is given its definite shape.

Figure 2:
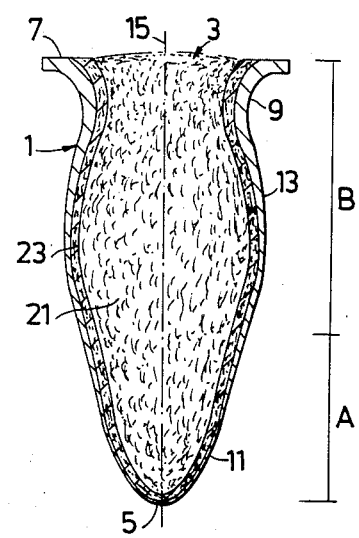

The ear plug illustrated in FIG. 2 has a deep-drawn sheath 1, e.g. of PUR Film, generally corresponding to that of the plug according to FIG. 1, but with the sheath thickness distribution beind different in so far as the thickness increases more uniformly from the tip 5 of the plug to its neck portion 9. The plug further has an elastic body 3 which is built up differently. The body 3 comprises a core 21 of foam plastics with a thin layer of fibrous material 23 surrounding the core, said material being of mineral fibres and here in the form of so-called glass down. The fibrous layer constitutes a low-friction layer, which facilitates relative movements between the sheath and the foam plastics material when the plug adjusts itself to the auditory meatus of an ear when being inserted therein. The volumetric weight of the foam plastics is between about 30 and 50 kg/m³.

It is quite simply possible to make a plug according to FIG. 1 with filling according to FIG. 2 and vice versa.

Figure 3:
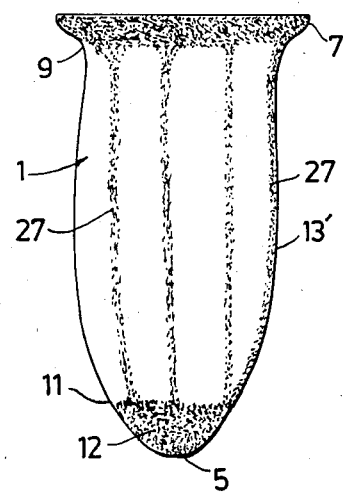
Figure 4:
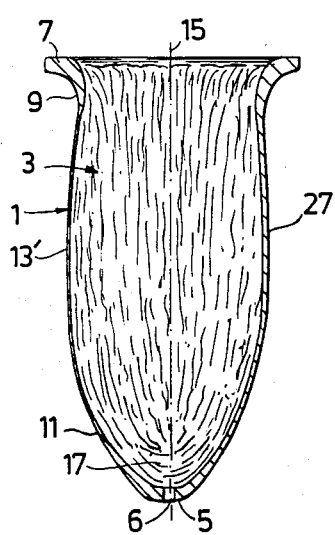

The ear plug illustrated in FIGS. 3 and 4 has a sheath 1, e.g. of deep-drawn PE film, enclosing a fibrous body 3 of the same kind as in FIG. 1. The plug has a substantially conically tapering forward portion terminating in a bluntly rounded tip 5, and a slightly outwardly curving or substantially cylindrical rear portion, which is thus more distinctly kept together. The forward portion constitutes approximately ¼ of the total plug length. The sheath 1 includes a forward portion 11, a rear portion 13' and a collar or flange 7. The plug has a suggestion of a neck portion 9 in conjunction with the flange 7. The sheath has substantially uniform thickness over the whole of the portion 11, 13' enclosing the body 3, excepting that the portion 12 of the sheath lying over the actual tip 5 has substantially greater thickness, and that the sheath has longitudinal rib portions 27 extending between and connecting the collar 7 and tip portion 12 and similarly having greater thickness. In FIG. 3 the thicker portions 7, 12 and 27 of the sheath 1 are denoted by shading. The general thickness of the sheath 1 is typically 5–10 μm, while the thickness at the collar or flange 7 is typically with the magnitude of 100 μm, in the area 12 typically with the magnitude of 80 μm and in the ribs typically with the magnitude of some tens of μm.

In FIG. 5 there is schematically illustrated the construction of an apparatus for producing an interconnected series of ear plugs in accordance with the invention, which in an advantageous way allows simple handling and packing of a large number of ear plugs. The main components of the apparatus are a mould sleeve 31, a preshaping member 32, a plunger 33 with associated guiding block 34, a supply plate or chute 35 for a glass down web 36, a cutting knife 37, a heat unit 38 for a plastics film strip 39 passing rectilinearly through the apparatus and from which the sheath 41 of the ear plugs 40 is thermoformed by deep-drawing in the mould sleeve, a punch pad 42 and a punch 43.

The mould sleeve 31 has a circular-cylindrical forming throughhole 45 for forming the sheath, and an upper, flat annular contact surface 46 for the plastics film 39, said surface joining onto the orifice of the forming hole 45 via a rounded edge 47. The mould sleeve 31 is disposed, in a manner not more closely described, for being displaceable vertically, as indicated by the double arrow 49, upwardly for bringing the sleeve into coaction with the pre-shaping member 32 arranged axially above, and downwardly for releasing an ear plug 40 produced in the mould sleeve. The pre-shaping member 32 has a circular-cylindrical pre-shaping throughhole 51, which is coaxial with the hole 45 and has the same diameter as the latter. At its top the pre-shaping hole 51 is expanded like a funnel, and opens out in a flat contact surface 52 running round the hole 51 for a square piece of glass down 53. The extension of the surface 52 corresponds to the glass down piece 53. For centering the piece 53 above the hole 51 the pre-shaping member 32 is provided on one or more sides with upstanding stop or locating members 54 at the edges of the surface 52. The lower portion of the pre-shaping member 32 is cylindrical, and at its lower outer edge it has an encircling stop projection 55 intended for coaction with the outer edge of the surface 46 of the mould sleeve 31, for clamping the plastics film strip 39 passing therebetween, when the mould sleeve is displaced upwards.

The plunger 33 is arranged coaxially with the hole 51 of the pre-shaping member 32 in a guide hole 57 in the guide block 34. The plunger has a diameter which is between about ⅓ and ½ of the diameter of the holes 45 and 51, and has a substantially flat end 58 with rounded edges. In a manner not more closely shown, the plunger is disposed for being thrust downwards (as indicated by the double arrow 59), sufficiently to press the glass down piece 53 through the pre-shaping hole down into the forming hole 45 as indicated by means of chain-dotted lines at 59, the piece 53 being formed into an elongate body, during passage through the pre-shaping hole 51, by being folded backwards and gathered around the end of the plunger 33, the plastics film strip between the mould sleeve 31 and member 32 being deep-drawn into a sheath 41 about the elongate body, when the latter is pressed down in the forming hole 45. Each glass down piece 53 is provided from the glass down web 36 in the chute 35, which is directed obliquely down towards the surface 52 to terminate a short distance therefrom, the web being fed in a way not shown in detail in the direction of the arrow 61 into engagement with the member 54, whereafter the cutting knife 37 cuts off the portion of the web 36 lying above the surface 52. The knife 37 is guided against a surface on the block 34 and coacts with an edge 63 on the pre-shaping member 32. The vertically reciprocal movement of the knife is indicated by the double arrow 65.

The heat unit 38 is disposed immediately before the mould sleeve 31, and has an upper and a lower portion between which passes the plastics film strip 39, the width of the strip somewhat exceeding the outside diameter of the mould sleeve 31. The heat unit is adapted for heating the central portion of the strip 39 to a width which somewhat falls below the inside diameter of the annular abutment 55. In this way the strip 39 will obtain unheated border areas, which facilitates its stepwise advance through the device with the aid of means not more closely shown. Heating can take place in an optional mode, e.g. by utilizing contact heat, convection heat, radiant heat or high frequency heat. A typical final temperature of the strip 39 when it leaves the unit 38 is about 170° C., when using PVC film, and about 130° C. when using PE film. With these temperatures in view, it can be suitable actively to cool the mould sleeve 31, e.g. by arranging channels in it for the passage of a cooling medium.

The punch pad 42 comprises a cylindrical sleeve with a throughhole 71, the diameter of which is somewhat larger than the greatest width of a manufactured plug 40. The hole 71 opens out with a rounded edge in an annular abutment surface 73 for the circular punch end 75 of the tubular punch 43. The punch end 75 is formed with teeth or the like, so that in co-action with the surface 73 it will give the flange or collar of the plug 40 an encircling tear-off line in the plastics film strip 39. The punch pad 42 is adapted movable, as indicated by the double arrow 77, to be moved up from below about a finished plug 40 dependent on the strip 39. The punch 43 is similarly movably arranged, as indicated by the double arrow 78, for being brought into contact with the pad 42.

The function of the described apparatus according to FIG. 5 is as follows, it being assumed that no plug has yet been produced and that a plastics film which shrinks, is utilized.

After the material web 36 has been fed forward and the knife 37 has cut off a piece 53 lying on the preshaping member, the piece is pressed by means of the plunger 33 through the member 32 down into the mould sleeve 31 (which is raised into coaction with the member 32), the heated plastics film portion retained between the member 32 and the mould sleeve 31 simultaneously being deep-drawn into a sheath 41 about the material piece 53, which has been gathered into an elastic body. After a certain time the sheath has cooled and has become fixed, shrinkage at the neck and flange portion having been obtained (not shown for the plug in the mould sleeve 31). The shrinkage is facilitated by the material piece 53 having such dimensions that the quantity of material at the neck portion of the plug is so small that compressibility there is very good. (The material at the neck portion consists of the corner portions of the square material piece 53).

The plunger 33 is now withdrawn, and the mould sleeve 31 is lowered so that the finished plug 40 is freely dependent from the strip 39. When the plug 40 is released from the mould sleeve 31 its cylindrical rear portion, when in the mould sleeve, will expand to its final outwardly curved form. The plastics film strip 39 with the plug 40 is now advanced a step, simultaneously as a new piece 53 is arranged on the pre-shaping member 32. The mould sleeve 31 is taken up again and the procedure described above is repeated to produce a second plug, subsequent to which a new advance is made (the punch pad 42 is assumed to be in the lowered position). After the mould sleeve 31 and punch pad 42 have been moved up into working position again, a new piece 53 is pressed down by the plunger 33 simultaneously as the punch 43 is lowered into engagement with the pad 42, the first-produced plug 40 in said pad being then provided with tear-off or fractural zones which allow it to be easily removed from the strip 39. The plunger 33 and punch 43 are now lifted up and the mould sleeve 31 and punch pad 42 are lowered, subsequent to which there is a new advance etc. The strip 39 with dependent produced plugs 40, fed out from the apparatus, is collected and suitable lengths of it may be removed and packed as desired. The produced plugs have, for example, the configuration illustrated in FIG. 1.

The apparatus illustrated in FIG. 5 can, of course, also be utilized for producing ear plugs of the kind illustrated in FIGS. 3 and 4, the perforations or holes 6 in the tip portion 5 of the produced plugs being suitably provided in the plastics film strip 39 at suitable intervals before the strip passes into the heat unit 38. A perforating device (indicated at 79 in FIG. 5) arranged under the path of the film strip can be utilized for perforation, this device including a vertically reciprocating perforating needle 80, the motion of which is controlled in time with the advance of the strip 39.

The embodiment of an apparatus in accordance with the invention illustrated in FIG. 6 differs from the embodiment according to FIG. 5 primarily in that the plug sheaths 41 are formed separately first, and thereafter filled with sound-damping material, and that the finished plugs are individually completely separated from the strip 39.

The apparatus illustrated has an endless series of mould sleeves 131 coupled to each other, each of which entirely corresponds to the mould sleeve 31 in the apparatus of FIG. 5, and of which three are shown. The mould sleeves 131 are disposed for stepwise circulation so that each sleeve in turn assumes a sheath forming position I immediately after the heat unit 38, a sheath filling position II below a pre-shaping member 32 with associated plunger 33, and a plug separating position III below a tubular punch 143. Positions I, II and III are in register with the line of advance of the strip 39 through the apparatus. After position III, the mould sleeves 131 pass a position (not shown) where the finished plugs 140 are removed from the respective mould sleeve in a suitable mode, whereafter the sleeves return by degrees to position I. The coupling between the mould sleeves is indicated at 81.

A die 83 is disposed above position I for forming the sheath, the die being axially in register with the forming hole 45 of the mould sleeve 131 in position I. The die has a die body 85 arranged on the end of a rod 86 vertically guided in a block 87. The die 83 is adapted for reciprocatory motion as indicated by the double arrow 89. The die body 85, intended for coaction with the forming hole 45 for deep-drawing an intermediate heated portion of the plastics film strip 39, has a conically tapering and bluntly rounded forward portion, and a cylindrical rear portion with a rounded rear end. The length of the die body 85 and the stroke downwards of the die 83 are selected such that the rear rounded end of the die body in the forming hole 45 will allow free shrinkage at the neck and collar portion of the formed sheath. The die body 85 consists of a soft felt material with an outward fibrous layer having low friction relative the material in the strip 39. The rear cylindrical portion of the die body 85 has a diameter substantially the same, or somewhat larger than the diameter of the forming hole 45. It is emphasized that the rear end of the die body can also be formed with a neck and collar portion corresponding to what is desired for the produced ear plugs, control of possible plastics film shrinkage in this portion thus being enabled.

The die 83 is adapted for passing through a locking sleeve 91 arranged above the mould sleeve 131 in position I, said locking sleeve 91 being provided downwardly with an annular projection 155, corresponding to the projection 55 on the member 32 in the apparatus according to FIG. 5, and intended for coaction with the surface 46 on the mould sleeve 131 during deep-drawing. The locking sleeve 91 is thus movably arranged as indicated by the double arrow 93. The insertion of elastic material in the ready sheath 41 in position II is done by utilizing the pre-shaping member 32 and plunger 33 in the same way as for the apparatus according to FIG. 5. However, the member 32 does not need to be provided here with any abutment projection for coaction with the underlying mould sleeve 131, since the ready sheath 41 has sufficient stability in the area joining on to the strip 39.

The material pieces 153 are advanced to the pre-shaping member 32 in a cut condition via an advancing chute or plate 135 with the aid of a pusher means 137, as indicated by the arrow 138. In the chute 137 there is a hole 139 through which the die 83 can pass. The material pieces 153 are provided by a material web 136 being advanced a suitable distance out over a plate 141, whereafter a cutting knife 146, arranged movably above the forward edge 143 of the plate and guided by a block 145, is lowered to cut the projecting material web piece by coaction with the edge 143 of the plate 141, the cut-off piece falling down onto the chute 135. The motion of the cutting knife 146 is indicated by the double arrow 165.

The material web 136 comprises foam plastics 147 with a thin layer 148 of mineral fibres on its underside. The layer 148 gives low friction, the displacement of the material web 136 and material pieces 153 and downward pressing of the pieces in the sheaths 41 via the pre-shaping member 32 being thus facilitated.

The punch 143 utilized for separating finished ear plugs 140 from the strip 39 corresponds entirely to the punch 43 in the apparatus according to FIG. 5, apart from its punch end 175 not having teeth or the like. The mould sleeves 131 perform the same function as the punch pad 42 in the apparatus according to FIG. 5.

With regard to the function of the apparatus, the operational movements downwards of the die 83, plunger 33 and punch 143 suitably take place simultaneously. After the formed sheath has been fixed and after withdrawal of said three members 83, 33 and 143, the mould sleeves 131 are advanced one step and a new material piece 153 is fed in. The advance of the mould sleeves 131 also involves a corresponding advance of the plastics film strip 39 from its storage means (not shown). The above-described sequence is then repeated. The used plastics film strip discharged from the apparatus, and containing holes corresponding to the ear plugs, can be easily collected, e.g. by allowing it to fall down into a container.

It is emphasized that all the driving and controlling means necessary for the movements of the different parts in the apparatuses according to FIGS. 5 and 6 easily can be implemented by any person skilled in the art, and therefore these means have not been shown or described. It should be further emphasized that the invention is not limited to the embodiments illustrated, but changes and modifications are possible within the scope of the following claims.

I claim:

1. A method of producing an ear plug having an elongate body of elastic material surrounded by a sheath of flexible plastics material which is intended for insertion in the auditory meatus of an ear, said method comprising:
    (a) shaping the elastic material into an elongate body about the free end of a plunger to form a die body;
    (b) deep drawing a thermoplastics film or foil into a sheath by means of the die body wherein the thermoplastic film or foil is deep drawn simultaneously as the elastic material is inserted into the sheath; and
    (c) removing the plunger while retaining the elastic material in the sheath.

2. The method of claim 1 wherein the thermoplastics film or foil is deep drawn by positioning the film or foil over a forming hole and pushing the die body with the film or foil into the forming hole.

3. A method of producing an ear plug having an elongate body of elastic material surrounded by a sheath of flexible plastics material which is intended for insertion in the auditory meatus of an ear, said method comprising:
    (a) positioning a thermoplastics film or foil over a forming hole;
    (b) pushing a plunger die with the film or foil into the forming hole to deep drawn the film or foil into a sheath having a shape substantially corresponding to the shape of the ear plug;
    (c) removing the plunger die from the forming hole; and
    (d) inserting the elastic material into the sheath while said sheath is in the forming hole.

4. The method of claim 3 wherein the elastic material is shaped into a elongate body about the free end of a plunger and said material is thrust with the aid of the plunger into the sheath obtained by deep-drawing.

5. The method of claim 4 wherein the elongate body of elastic material formed on the plunger has an outer layer having low friction in relation to the sheath for facilitating the insertion of the elongate body into the sheath.

6. The method of claim 3 wherein the elastic material is inserted by storing pieces thereof in a plunger which is moved down into the sheath, the pieces then being pressed out into the sheath and the plunger removed therefrom.

7. The method of claim 5 wherein the low friction outer layer is fibrous material.

8. The method of claim 3 wherein the end of the plunger die has a die body comprising a soft material with an outer low friction layer and has a forward conically tapered portion with a bluntly rounded tip and a rear portion which is substantially cylindrical with a diameter at least substantially the same as the diameter of the forming hole.

* * * * *